(12) United States Patent
Bredsguard

(10) Patent No.: US 8,716,206 B2
(45) Date of Patent: *May 6, 2014

(54) ACETIC ACID-CAPPED ESTOLIDE BASE OILS AND METHODS OF MAKING THE SAME

(71) Applicant: Biosynthetic Technologies, LLC, Irvine, CA (US)

(72) Inventor: Jakob Bredsguard, Lake Forest, CA (US)

(73) Assignee: Biosynthetic Technologies, LLC, Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/865,520

(22) Filed: Apr. 18, 2013

(65) Prior Publication Data

US 2013/0245298 A1   Sep. 19, 2013

Related U.S. Application Data

(63) Continuation of application No. 13/223,008, filed on Aug. 31, 2011, now Pat. No. 8,455,412.

(60) Provisional application No. 61/498,499, filed on Jun. 17, 2011, provisional application No. 61/378,891, filed on Aug. 31, 2010.

(51) Int. Cl.
    *C07C 69/34* (2006.01)

(52) U.S. Cl.
    USPC ........................................ 508/465

(58) Field of Classification Search
    USPC ........................................ 508/465
    See application file for complete search history.

(56) References Cited

U.S. PATENT DOCUMENTS

| | | |
|---|---|---|
| 2,049,072 A | 7/1936 | Mikeska et al. |
| 2,652,411 A | 9/1953 | Teeter et al. |
| 2,862,884 A | 12/1958 | Dilworth et al. |
| 3,299,110 A | 1/1967 | Pine |
| 4,428,850 A | 1/1984 | Zoleski et al. |
| 4,431,673 A | 2/1984 | Goldner et al. |
| 4,567,037 A | 1/1986 | Ciaudelli |
| 4,639,369 A | 1/1987 | Ciaudelli |
| 4,806,572 A | 2/1989 | Kellett |
| 4,867,965 A | 9/1989 | Ciaudelli |
| 5,011,629 A * | 4/1991 | Bilbo ............ 554/122 |
| 5,204,375 A | 4/1993 | Kusakawa et al. |
| 5,380,894 A | 1/1995 | Burg et al. |
| 5,451,332 A | 9/1995 | Lawate |
| 5,518,728 A | 5/1996 | Burdzy et al. |
| 5,658,863 A | 8/1997 | Duncan et al. |
| 6,018,063 A | 1/2000 | Isbell et al. |
| 6,160,144 A | 12/2000 | Bongardt et al. |
| 6,316,649 B1 | 11/2001 | Cermak et al. |
| 7,252,779 B2 | 8/2007 | Mosier et al. |
| 7,651,641 B2 | 1/2010 | Corkran et al. |
| 7,666,828 B2 | 2/2010 | Bernhardt et al. |
| 8,236,194 B1 | 8/2012 | Bredsguard et al. |
| 8,258,326 B1 | 9/2012 | Forest et al. |
| 8,268,199 B1 | 9/2012 | Forest et al. |
| 8,287,754 B1 | 10/2012 | Bredsguard et al. |
| 8,372,301 B2 | 2/2013 | Bredsguard et al. |
| 8,399,389 B2 | 3/2013 | Bredsguard et al. |
| 8,404,867 B2 | 3/2013 | Forest et al. |
| 8,450,256 B2 | 5/2013 | Bredsguard |
| 8,512,592 B2 | 8/2013 | Forest et al. |
| 2002/0017629 A1 | 2/2002 | Mosier et al. |
| 2002/0193262 A1 | 12/2002 | Kaimai et al. |
| 2004/0046146 A1 | 3/2004 | Ankner et al. |
| 2007/0092475 A1 | 4/2007 | Wohlman |

(Continued)

FOREIGN PATENT DOCUMENTS

| | | |
|---|---|---|
| EP | 0 665 284 A2 | 8/1995 |
| FR | 2906530 A1 | 4/2008 |

(Continued)

OTHER PUBLICATIONS

Aguieiras et al., "Estolide Synthesis Catalyzed by Immobilized Lipases," *Enzyme Research*, ID432746, 1-7 (2011).
Biresaw et al., "Film-forming properties of estolides," *Tribology Letters*, 27(1): 69-78 (2007).
Brutting et al., "Produkte der Dimerisierung ungesattigter Fettsauren X: Identifizierung von Estoliden in der Anfangsphase der Dimerisierung," *Fat Sci. Technol.*, 95(5): 193-99 (1993).

(Continued)

*Primary Examiner* — Taiwo Oladapo
(74) *Attorney, Agent, or Firm* — Jeremy Forest

(57) ABSTRACT

Provided herein are compounds, including those of the Formula II

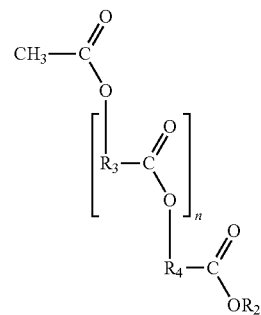

in which n is an integer equal to or greater than 1; $R_2$, is selected from hydrogen and optionally substituted alkyl that is saturated or unsaturated, and branched or unbranched; and $R_3$, and $R_4$, independently for each occurrence, are selected from optionally substituted alkyl that is saturated or unsaturated, and branched or unbranched. Also provided are compositions containing such compounds and methods of making both compounds and compositions thereof.

18 Claims, No Drawings

(56) References Cited

U.S. PATENT DOCUMENTS

| | | |
|---|---|---|
| 2007/0161832 A1 | 7/2007 | Myllyoja et al. |
| 2008/0020956 A1 | 1/2008 | Mosier et al. |
| 2009/0012324 A1 | 1/2009 | Choi et al. |
| 2009/0159835 A1 | 6/2009 | Kramer et al. |
| 2009/0159837 A1 | 6/2009 | Kramer et al. |
| 2010/0120643 A1 | 5/2010 | Brown et al. |
| 2010/0184855 A1 | 7/2010 | Bernhardt et al. |
| 2010/0292328 A1 | 11/2010 | Althaus et al. |
| 2011/0092723 A1 | 4/2011 | Rosas et al. |
| 2011/0105814 A1 | 5/2011 | Koivusalmi et al. |
| 2011/0294174 A1 | 12/2011 | Franklin et al. |
| 2012/0018667 A1 | 1/2012 | Krammer et al. |
| 2012/0083435 A1 | 4/2012 | Bredsguard |
| 2012/0136168 A1 | 5/2012 | Kersbulck et al. |
| 2012/0172269 A1 | 7/2012 | Greaves et al. |
| 2012/0172609 A1 | 7/2012 | Bredsguard et al. |
| 2012/0178660 A1 | 7/2012 | Bredsguard |
| 2012/0322707 A1 | 12/2012 | Bredsguard et al. |
| 2013/0053589 A1 | 2/2013 | Forest et al. |
| 2013/0065970 A1 | 3/2013 | Bredsguard et al. |

FOREIGN PATENT DOCUMENTS

| | | |
|---|---|---|
| JP | 7228881 | 8/1995 |
| WO | WO-99/25794 | 5/1999 |
| WO | WO-01/53247 A1 | 7/2001 |
| WO | WO-2008/040864 A1 | 4/2008 |
| WO | WO-2009/139003 A1 | 11/2009 |
| WO | WO-2011/037778 A1 | 3/2011 |
| WO | WO-2011/106186 A1 | 9/2011 |

OTHER PUBLICATIONS

Cermak et al., "Synthesis of Estolides from Oleic and Saturated Fatty Acids," *JAOCS*, 78(6): 557-65 (2001).

Cermak et al., "Physical properties of saturated estolides and their 2-ethylhexyl esters," 16: 119-27 (2002).

Cermak et al., "Synthesis and physical properties of estolide-based functional fluids," *Indus. Crops and Prods.*, 18: 183-96 (2003).

Cermak et al., "Improved oxidative stability of estolide esters," *Indus. Crops and Prods.*, 18: 223-30 (2003).

Cermak et al., "Synthesis and Physical Properties of Cuphea-Oleic Estolides and Esters," *JAOCS*, 81(3): 297-303 (2004).

Cermak et al., "Synthesis and physical properties of estolides from lesquerella and castor fatty acid esters," *Indus. Crops and Prods.*, 23: 256-63 (2006).

Cermak et al., "Synthesis and Physical Properties of Tallow-Oleic Estolide 2-Ethylhexyl Esters," *J. Amer. Oil Chem. Soc.*, 84(5): 449-56 (2007).

Cermak et al., "Synthesis and physical properties of mono-estolides with varying chain lengths," *Indus. Crops and Prods.*, 29: 205-13 (2009).

Choi et al., "Iron-catalysed green synthesis of carboxylic esters by the intermolecular addition of carboxylic acids to alkenes," *Chem. Commun.*, pp. 777-779 (2008).

Erhan et al., "Estolide Production with Modified Clay Catalysts and Process Conditions," *JAOCS*, 74(3): 249-54 (1997).

Erhan et al., "Biodegradation of Estolides from Monounsaturated Fatty Acids," *JAOCS*, 74(5): 605-07 (1997).

Teeter et al., "Synthetic Lubricants from Hydroxystearic Acids," *Indus. and Eng. Chem.*, 45(8): 1777-79 (1953).

Gast et al., "Synthetic Lubricants from Polyhydroxystearic Acids," *Indus. and Eng. Chem.*, 46(10): 2205-08 (1954).

Harry-O'Kuru et al., "Synthesis of Estolide Esters from cis-9-Octadecanoic Acid Estolides," *JAOCS*, 78(3): 219-23 (2001).

Isbell et al., "Acid-Catalyzed Condensation of Oleic Acid into Estolides and Polyestolides," *JAOCS*, 71(2): 169-74 (1994).

Isbell et al., "Characterization of Estolides Produced from Acid-Catalyzed Condensation of Oleic Acid," *JAOCS*, 71(4): 379-83 (1994).

Isbell et al., "Optimization of the Sulfuric Acid-Catalyzed Estolide Synthesis from Oleic Acid," *JAOCS*, 74(4): 473-76 (1997).

Isbell et al., "Physical properties of estolides and their ester derivatives," *Indus. Crops and Prods.*, 13: 1120 (2001).

Mathers et al., "A General Polymerization Method Using Hydoralkoxylation and Hydrocarboxylation Reactions Catalyzed by Triflic Acid," *Macromolecules*, 41, 524-526 (2008).

Nordin et al., "New Silica Supported $HClO_4$ as Efficient Catalysts for Estolide Synthesis from Oleic Acid," *Adv. Mat. Res.*, 173: 140-45 (2011).

Rudnick, L. R., *Synthetics, Mineral Oils, and Bio-Based Lubricants*, CRC Press, Boca Raton, FL.; Chap. 22, pp. 371-374 (2006).

Salimon et al., "Synthesis and Physical Properties of Estolide Ester Using Saturated Fatty Acid and Ricinoleic Acid," *J. Auto. Methods and Manag. Chem.*, ID263624,1-4 (2011).

Zerkowski, J., "Estolides: From structure and function to structured and functionalized," *Lipid Tech.*, 20(11): 253-56 (2008).

Abstract of JP 7228881, published Aug. 29, 1995.

Erhan et al., "Estolides from Meadowfoam Oil Fatty Acids and Other Monounsaturated Fatty Acids," *JAOCS*, 70:5, 461-465 (May 1993).

Kulkarni et al., "Kinetics of the Catalytic Esterification of Castor Oil with Lauric Acid Using n-Butyl Benzene as a Water Entrainer," *JAOCS*, 80:10, 1033-1038 (2003).

Kwie et al., "Bismuth (III) Triflate: A Safe and Easily Handled Precursor for Triflic Acid: Application to the Esterification Reaction," *Syn. Comm.*, 40: 1082-1087 (2010).

Lotero et al., "Synthesis of Biodiesel via Acid Catalysis," *Ind. Eng. Chem.*, 44: 5353-5363 (2005).

Ishihara et al., "Direct Condensation of Carboxylic Acids with Alcohols Catalyzed by Hafnium (IV) Salts," *Science*, 290: 1140-1142 (2000).

Isbell et al., "Physical properties of triglyceride estolides from lesquerella and castor oils," *Indus. Crops and Prods.*, 23: 256-253 (2006).

Tomoda et al., "Characteristic Properties of Cutting Fluid Additives Derived From the Reaction Products of Hydroxyl Fatty Acids With Some Acid Anhydrides," *J. of Surf. and Deter.*, 1:4, 533-537 (Oct. 1998).

Simonsick et al., "Details structural elucidation of polyesters and acrylates using Fourier transform mass spectroscopy," *Anal. Bioanal. Chem.*, 392: 575-583 (2008).

International Search Report and Written Opinion mailed Nov. 30, 2011 in International Application No. PCT/US2011/001537.

International Search Report and Written Opinion mailed Nov. 23, 2011 in International Application No. PCT/US2011/050102.

Written Opinion of the International Preliminary Examining Authority for counterpart application PCT/US2011/001537, filed Aug. 31, 2011.

International Preliminary Report on Patentability for counterpart application PCT/US2011/001537, mailed Mar. 5, 2013.

Written Opinion of the International Preliminary Examining Authority for counterpart application PCT/US2011/050102, filed Aug. 31, 2011.

International Preliminary Report on Patentability for counterpart application PCT/US2011/050102, mailed Mar. 5, 2013.

International Search Report and Written Opinion mailed Nov. 23, 2011 in International Application No. PCT/US2011/001540.

International Search Report and Written Opinion mailed Apr. 11, 2012 in International Application No. PCT/US2012/023933.

International Search Report and Written Opinion mailed May 15, 2012 in International Application No. PCT/US2012/026887.

International Search Report and Written Opinion mailed Apr. 26, 2012 in International Application No. PCT/US2012/024260.

International Search Report and Written Opinion for international application PCT/US2012/026538, mailed Apr. 26, 2012.

Article 19 Amendments and Letter Accompanying Replacement Sheets for international application PCT/US2012/026538, filed May 17, 2012.

Informal Comments filed in response to International Search Report and Written Opinion for international application PCT/US2012/026538, filed May 17, 2012.

(56) References Cited

OTHER PUBLICATIONS

International Search Report and Written Opinion for counterpart application PCT/US2012/039937, mailed Aug. 6, 2012.
Co-Pending U.S. Appl. No. 13/766,138, filed Feb. 13, 2013.
Co-Pending U.S. Appl. No. 13/754,775, filed Jan. 30, 2013.
Co-Pending U.S. Appl. No. 13/705,543, filed Dec. 5, 2012.
Cermak et al., "Synthesis and Physical Properties of New Estolide Esters", *Industrial Crops and Products*, 46: 386-391 (2013).
Cermak et al., "Comparison of a New Estolide Oxidative Stability Package," *J. Am. Oil Chem. Soc.*, 85: 879-885 (2008).
Garcia-Zapateiro et al., "Viscous, thermal and tribological characterization of oleic and ricinoleic acids-derived estolides and their blends with vegetable oils", *Journal of Indus. and Engin. Chem.*, 19: 1289-1298 (2013).
Co-Pending U.S. Appl. No. 13/936,015, filed Jul. 5, 2013.
Co-Pending U.S. Appl. No. 13/950,508, filed Jul. 25, 2013.
Office Action dated Jan. 17, 2013, for U.S. Appl. No. 13/223,008, filed Aug. 31, 2011.
Notice of Allowance dated Apr. 15, 2013, for U.S. Appl. No. 13/223,008, filed Aug. 31, 2011.

* cited by examiner

ACETIC ACID-CAPPED ESTOLIDE BASE OILS AND METHODS OF MAKING THE SAME

CROSS-REFERENCE TO RELATED APPLICATIONS

This application is a continuation of U.S. patent application Ser. No. 13/223,008, filed Aug. 31, 2011, now U.S. Pat. No. 8,455,412, which claims the benefit under 35 U.S.C. §119(e) of U.S. Provisional Patent Application No. 61/498,499, filed Jun. 17, 2011, and U.S. Provisional Patent Application No. 61/378,891, filed Aug. 31, 2010, which are incorporated herein by reference in their entireties for all purposes.

STATEMENT REGARDING FEDERALLY SPONSORED RESEARCH

The subject of this invention was made with support under U.S. Department of Agriculture—Agricultural Research Service Cooperative Research and Development Agreement (CRADA) Nos. 58-3K95-1-1508-M and 58-3K95-6-1147. Accordingly, the government may have certain rights in this invention.

FIELD

The present disclosure relates to acetic acid-capped estolides and methods of making the same. The estolides described herein may be suitable for use as biodegradable oil base stocks and lubricants.

BACKGROUND

Synthetic esters such as polyol esters and adipates, low viscosity poly alpha olefins (PAO) such as PAO 2, and vegetable oils such as canola oil and oleates have been described for use industrially as biodegradable base stocks to formulate lubricants. Such base stocks may be used in the production of lubricating oils for automotives, industrial lubricants, and lubricating greases. Finished lubricants typically comprise the base oil and additives to help achieve the desired viscometric properties, low temperature behavior, oxidative stability, corrosion protection, demulsibility and water rejection, friction coefficients, lubricities, wear protection, air release, color and other properties. However, it is generally understood that biodegradability cannot be improved by using common additives that are available in today's marketplace. For environmental, economical, and regulatory reasons, it is of interest to produce biodegradable lubricating oils, other biodegradable lubricants, and compositions including lubricating oils and/or lubricants, from renewable sources of biological origin.

Estolides present a potential source of biobased, biodegradable oils that may be useful as lubricants and base stocks. Several estolide synthetic processes have been previously described, such as the homopolymerization of castor oil fatty acids or 12-hydroxystearic acid under thermal or acid catalyzed conditions, as well as the production of estolides from unsaturated fatty acids using a high temperature and pressure condensation over clay catalysts. Processes for the enzymatic production of estolides from hydroxy fatty acids present in castor oil using lipase have also been described.

In U.S. Pat. No. 6,018,063, Isbell et al. described estolide compounds derived from oleic acids under acidic conditions and having properties for use as lubricant base stocks, wherein the "capping" fatty acid comprises oleic or stearic acid. In U.S. Pat. No. 6,316,649, Cermak et al. reported estolides derived from oleic acids and having capping materials derived from $C_6$ to $C_{14}$ fatty acids. Neither Isbell et al. nor Cermek et al., however, describes the preparation of estolides comprising $C_2$ fatty acid capping materials.

SUMMARY

Described herein are estolide compounds, estolide-containing compositions, and methods of making the same. In certain embodiments, such compounds and/or compositions may be useful as base oils and lubricants. In certain embodiments, the estolides comprise at least one compound of Formula I:

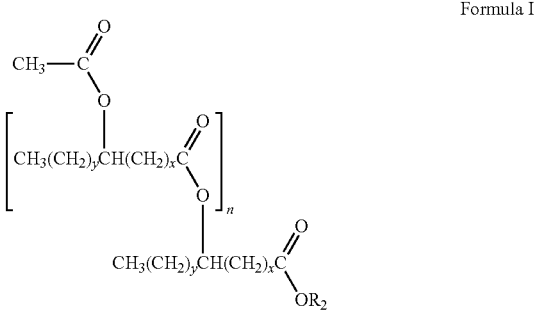

Formula I wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is an integer selected from 1, 2, 3, 4, 5, 6, 7, 8, 9, 10, 11, and 12; and
$R_2$ is selected from hydrogen and optionally substituted alkyl that is saturated or unsaturated, and branched or unbranched;
wherein each fatty acid chain residue of said at least one compound is independently optionally substituted.

In certain embodiments, the estolide compounds comprise at least one compound of Formula II:

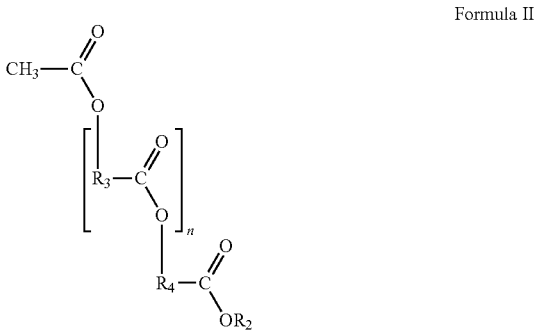

Formula II wherein
n is an integer selected from 1, 2, 3, 4, 5, 6, 7, 8, 9, 10, 11, and 12;
$R_2$ is selected from hydrogen and optionally substituted alkyl that is saturated or unsaturated, and branched or unbranched; and R₃ and R₄, independently for each occurrence, are selected from optionally substituted alkyl that is saturated or unsaturated, and branched or unbranched.

In certain embodiments, the estolide compounds comprise at least one compound of Formula III:

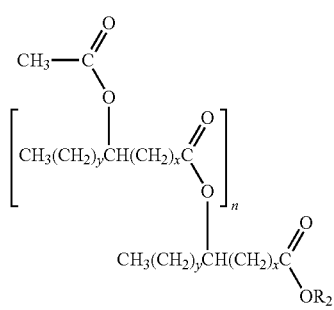

Formula III wherein
x is, independently for each occurrence, an integer selected from 0 to 20;
y is, independently for each occurrence, an integer selected from 0 to 20;
n is an integer greater than or equal to 1; and
R₂ is selected from hydrogen and optionally substituted alkyl that is saturated or unsaturated, and branched or unbranched;
wherein each fatty acid chain residue of said at least one compound is independently optionally substituted.

DETAILED DESCRIPTION

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH₂ is attached through the carbon atom.

"Alkoxy" by itself or as part of another substituent refers to a radical —OR³¹ where R³¹ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp³ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

"Compounds" refers to compounds encompassed by structural Formula I, II, and III herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I, II, and III include, but are not limited to, optical isomers of compounds of Formula I, II, and III, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I, II, and III cover all asymmetric variants of the compounds described herein, including isomers, racemates, enantiomers, diastereomers, and other mixtures thereof. In addition, compounds of Formula I, II, and III include Z- and E-forms (e.g., cis- and trans-forms) of compounds with double bonds. The compounds of Formula I, II, and III may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or $sp^3$ carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or sp$^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, —R$^{64}$, —R$^{60}$, —O$^-$, —OH, =O, —OR$^{60}$, —SR$^{60}$, —S$^-$, =S, —NR$^{60}$R$^{61}$, =NR$^{60}$, —CN, —CF$_3$, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, NR$^{62}$C(S)NR$^{60}$R$^{61}$, —NR$^{62}$C(NR$^{63}$)NR$^{60}$R$^{61}$, —C(NR$^{62}$)NR$^{60}$R$^{61}$, —S(O)$_2$, NR$^{60}$R$^{61}$, —NR$^{63}$S(O)$_2$R$^{60}$, NR$^{63}$C(O)$_R$$^{60}$, and S(O)R$^{60}$;

wherein each —R$^{64}$ is independently a halogen; each R$^{60}$ and R$^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or R$^{60}$ and R$^{61}$ together with the nitrogen atom to which they are bonded form a heterocycloalkyl, substituted heterocycloalkyl, heteroaryl, or substituted heteroaryl ring, and R$^{62}$ and R$^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or R$^{62}$ and R$^{63}$ together with the atom to which they are bonded form one or more heterocycloalkyl, substituted heterocycloalkyl, heteroaryl, or substituted heteroaryl rings;

wherein the "substituted" substituents, as defined above for R$^{60}$, R$^{61}$, R$^{62}$, and R$^{63}$, are substituted with one or more, such as one, two, or three, groups independently selected from alkyl, -alkyl-OH, —O-haloalkyl, -alkyl-NH$_2$, alkoxy, cycloalkyl, cycloalkylalkyl, heterocycloalkyl, heterocycloalkylalkyl, aryl, heteroaryl, arylalkyl, heteroarylalkyl, —O$^-$, —OH, =O, —O-alkyl, —O-aryl, —O-heteroarylalkyl, —O-cycloalkyl, —O-heterocycloalkyl, —SH, —S$^-$, =S, —S-alkyl, —S-aryl, —S-heteroarylalkyl, —S-cycloalkyl, —S-heterocycloalkyl, —NH$_2$, =NH, —CN, —CF$_3$, —OCN, —SCN, —NO, —NO$_2$, =N$_2$, —N$_3$, —S(O)$_2$O$^-$, —S(O)$_2$, —S(O)$_2$OH, —OS(O$_2$)O$^-$, —SO$_2$ (alkyl), —SO$_2$(phenyl), —SO$_2$(haloalkyl), —SO$_2$NH$_2$, —SO$_2$NH(alkyl), —SO$_2$NH(phenyl), —P(O)(O$^-$)$_2$, —P(O)(O-alkyl)(O$^-$), —OP(O)(O-alkyl)(O-alkyl), —CO$_2$H, —C(O)O(alkyl), —CON(alkyl)(alkyl), —CONH(alkyl), —CONH$_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

All numerical ranges herein include all numerical values and ranges of all numerical values within the recited range of numerical values.

The present disclosure relates to estolide compounds, compositions, and methods of making the same. In certain embodiments, the present disclosure relates to biosynthetic estolides having certain desired viscometric properties, while retaining or even improving other properties such as oxidative stability and pour point. In certain embodiments, the present disclosure relates to new methods of preparing estolide compounds exhibiting such properties. The present disclosure also relates to compositions comprising acetic acid-capped estolides and their formulations.

In certain embodiments the composition comprises at least one compound of Formula I:

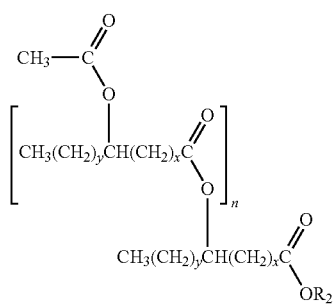

Formula I wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is an integer selected from 1, 2, 3, 4, 5, 6, 7, 8, 9, 10, 11, and 12; and
R$_2$ is selected from hydrogen and optionally substituted alkyl that is saturated or unsaturated, and branched or unbranched;
wherein each fatty acid chain residue of said at least one compound is independently optionally substituted.

The terms "chain" or "fatty acid chain" or "fatty acid chain residue," as used with respect to the estolide compounds of Formula I, II, and III, refer to one or more of the fatty acid residues incorporated in estolide compounds, e.g., R$_3$ or R$_4$ of Formula II, or the structures represented by CH$_3$(CH$_2$)$_y$CH(CH$_2$)$_x$C(O)O— in Formulas I and III.

The acetyl group (CH$_3$C(O)O—) in Formula I, II, and III at the top of each Formula shown is an example of what may be referred to as a "cap" or "capping material," as it "caps" the top of the estolide. Similarly, the capping group may be an organic acid residue of general formula —OC(O)-alkyl, i.e., a carboxylic acid with an substituted or unsubstituted, saturated or unsaturated, and/or branched or unbranched alkyl as defined herein. In certain embodiments, the "cap" or "capping group" is a fatty acid. In certain embodiments, the capping group, regardless of size, is substituted or unsubstituted, saturated or unsaturated, and/or branched or unbranched. The cap or capping material may also be referred to as the primary or alpha ($\alpha$) chain.

Depending on the manner in which the estolide is synthesized, the cap or capping group alkyl may be the only alkyl from an organic acid residue in the resulting estolide that is unsaturated. In certain embodiments, it may be desirable to use a saturated organic or fatty-acid cap to increase the overall saturation of the estolide and/or to increase the resulting estolide's stability. For example, in certain embodiments it may be desirable to provide a method of providing a saturated capped estolide by hydrogenating an unsaturated cap using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The R$_4$C(O)O— of Formula II or structure CH$_3$(CH$_2$)$_y$CH(CH$_2$)$_x$C(O)O— of Formula I and III serve as the "base" or "base chain residue" of the estolide. Depending on the manner in which the estolide is synthesized, the base organic acid or fatty acid residue may be the only residue that remains in its free-acid form after the initial synthesis of the estolide. However, in certain embodiments, in an effort to alter or improve the properties of the estolide, the free acid may be reacted with any number of substituents. For example, it may be desirable to react the free acid estolide with alcohols, glycols, amines, or other suitable reactants to provide the corresponding ester, amide, or other reaction products. The base or base chain residue may also be referred to as tertiary or gamma ($\gamma$) chains.

The R$_3$C(O)O— of Formula II or the structure CH$_3$(CH$_2$)$_y$CH(CH$_2$)$_x$C(O)O— of Formula I and III are linking residues that link the capping material and the base fatty-acid residue. There may be any number of linking residues in the estolide, including when n=0 and the estolide is in its dimer form. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic group of another fatty acid. In some embodiments, it may be desirable to have a linking fatty acid that is monounsaturated so that when the fatty acids link together, all of the sites of unsaturation are eliminated. The linking residue(s) may also be referred to as secondary or beta ($\beta$) chains.

In certain embodiments, the cap is an acetyl group, the linking residue(s) is one or more fatty acid residues, and the base chain residue is a fatty acid residue. In certain embodiments, the linking residues present in an estolide differ from one another. In certain embodiments, one or more of the linking residues differs from the base chain residue.

As noted above, in certain embodiments, suitable unsaturated fatty acids for preparing the estolides may include any mono- or polyunsaturated fatty acid. For example, monounsaturated fatty acids, along with a suitable catalyst, will form a single carbocation of the addition of a second fatty acid, whereby a single link between two fatty acids is formed. Suitable monounsaturated fatty acids may include, but are not limited to, palmitoleic (16:1), vaccenic (18:1), oleic acid (18:1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24:5), tetracosahexaenoic acid (24:6), linoleic acid (18:2), gamma-linoleic acid (18:3), eicosadienoic acid (20:2), dihomo-gamma-linolenic acid (20:3), arachidonic acid (20:4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic (18:3), catalpic acid (18:3), punicic acid (18:3), rumelenic acid (18:3), alpha-parinaric acid (18:4), beta-parinaric acid (18:4), and bosseopentaenoic acid (20:5).

The process for preparing the estolide compounds described herein may include the use of any natural or synthetic fatty acid source. However, it may be desirable to source the fatty acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel based materials and other sources of the materials desired.

In some embodiments, the estolide comprises fatty-acid chains of varying lengths. In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, y is, independently for each occurrence, an integer selected from 0, 1, 2, 3, 4, 5, 6, 7, 8, 9, 10, 11, 12, 13, 14, 15, 16, 17, 18, 19, and 20.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y is 15. In some embodiments, x+y is, independently for each chain, an integer selected from 6, 7, 8, 9, 10, 11, 12, 13, 14, 15, 16, 17, 18, 19, 20, 21, 22, 23, and 24.

In some embodiments, the estolide compound of Formula I, II, and III may comprise any number of fatty acid residues to form an "n-mer" estolide. For example, the estolide may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is 1, wherein said at least one compound of Formula I, II, and III comprises the trimer. In some embodiments, n is an integer that is equal to or greater than 1. In some embodiments, n is an integer that is equal to or greater than 10. In some embodiments, n is an integer selected from 0 to 20. In some embodiments, n is an integer selected from 1 to 12, 1 to 8, or 1 to 4. In some embodiments, n is an integer selected from 0, 1, 2, 3, 4, 5, 6, 7, 8, 9, 10, 11, 12, 13, 14, 15, 16, 17, 18, 19, and 20.

In some embodiments, $R_2$ of Formula I, II, or III is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_2$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_2$ is selected from $C_{13}$ to $C_{17}$ alkyl, such as from $C_{13}$ alkyl, $C_{15}$ alkyl, and $C_{17}$ alkyl. In some embodiments, $R_2$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_3$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_3$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_3$ is selected from $C_{13}$ to $C_{17}$ alkyl, such as from $C_{13}$ alkyl, $C_{15}$ alkyl, and $C_{17}$ alkyl. In some embodiments, $R_3$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ alkyl.

In some embodiments, $R_4$ is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{18}$ alkyl. In some embodiments, the alkyl group is selected from $C_7$ to $C_{17}$ alkyl. In some embodiments, $R_4$ is selected from $C_7$ alkyl, $C_9$ alkyl, $C_{11}$ alkyl, $C_{13}$ alkyl, $C_{15}$ alkyl, and $C_{17}$ alkyl. In some embodiments, $R_4$ is selected from $C_{13}$ to $C_{17}$ alkyl, such as from $C_{13}$ alkyl, $C_{15}$ alkyl, and $C_{17}$ alkyl. In some embodiments, $R_4$ is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{2-2}$ alkyl.

In some embodiments, the estolides of Formula I, II, and III may be in their free-acid form, wherein $R_2$ is hydrogen. In some embodiments, $R_2$ is selected from optionally substituted alkyl that is saturated or unsaturated, and branched or unbranched. The $R_2$ residue may comprise any desired alkyl group, such as those derived from esterification of the estolide with the alcohols identified in the examples herein. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ may be selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, $R_2$ may be branched, such as isopropyl, isobutyl, or 2-ethylhexyl. In some embodiments, $R_2$ may be a larger alkyl group, branched or unbranched, comprising $C_{12}$ alkyl, $C_{16}$ alkyl, $C_{18}$ alkyl, or $C_{20}$ alkyl. Such groups at the $R_2$ position may be derived from esterification of the free-acid estolide using the Jarcoff line of alcohols marketed by Jarchem Industries, Inc. of Newark, N.J., including Jarcoff I-18CG, 1-20, 1-12, 1-16, I-18T, and 85BJ. In some cases, $R_2$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the estolides described herein may comprise highly-branched isopalmityl or isostearyl groups at the $R_2$ position, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in certain embodiments, large, highly-branched alkyl groups (e.g., isopalmityl and isostearyl) at the $R_2$ position of the estolides can provide at least one way to increase the lubricant's viscosity, while substantially retaining or even reducing its pour point.

In some embodiments, the compounds described herein may comprise a mixture of two or more estolide compounds of Formula I, II, and III. It is possible to characterize the chemical makeup of an estolide, a mixture of estolides, or a composition comprising estolides by using the compound's, mixtures's, or composition's, measured estolide number (EN). The EN of an estolide represents the average number of fatty acids added to the base fatty acid. The EN also represents the average number of estolide linkages per molecule:

$$EN = n+1$$

wherein n is the number of secondary (β) fatty acids. Accordingly, a single estolide compound will have an EN that is a whole number, for example for dimers, trimers, and tetramers:

$$\text{dimer } EN = 1$$

$$\text{trimer } EN = 2$$

$$\text{tetramer } EN = 3$$

However, a composition comprising two or more estolide compounds may have an EN that is a whole number or a fraction of a whole number. For example, a composition having a 1:1 molar ratio of dimer and trimer would have an EN of 1.5, while a composition having a 1:1 molar ratio of tetramer and trimer would have an EN of 2.5.

In some embodiments, the compositions may comprise a mixture of two or more estolides having an EN that is an integer or fraction of an integer that is greater than or equal to 1. In some embodiments, the EN may be an integer or fraction of an integer selected from about 1.0 to about 5.0. In some embodiments, the EN is an integer or fraction of an integer selected from 1.2 to about 4.5. In some embodiments, the estolide compounds described herein will be in there trimer form or larger, wherein the EN is greater than or equal to 2. Thus, in some embodiments, the EN is selected from an integer or fraction of an integer that is from about 2.0 to about 3.0, or from about 2.2 to about 2.8. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0. In some embodiments, the EN is selected from 1, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. In some embodiments the estolides described herein may comprise at least one compound of Formula II:

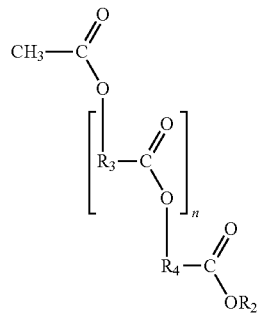

Formula II wherein
n is an integer greater than or equal to 1;
$R_2$ is selected from hydrogen and optionally substituted alkyl that is saturated or unsaturated, and branched or unbranched; and
$R_3$ and $R_4$, independently for each occurrence, are selected from optionally substituted alkyl that is saturated or unsaturated, and branched or unbranched.

In some embodiments, n is an integer selected from 1 to 20. In some embodiments, n is an integer selected from 1 to 12. In some embodiments, n is an integer selected from 1, 2, 3, 4, 5, 6, 7, 8, 9, 10, 11, 12, 13, 14, 15, 16, 17, 18, 19 and 20. In some embodiments, one or more $R_3$ differs from one or more other $R_3$ in a compound of Formula II. In some embodiments, one or more $R_3$ differs from $R_4$ in a compound of Formula II. In some embodiments, if the compounds of Formula II are prepared from one or more polyunsaturated fatty acids, it is possible that one or more of $R_3$ and $R_4$ will have one or more sites of unsaturation. In some embodiments, if the compounds of Formula II are prepared from one or more branched fatty acids, it is possible that one or more of $R_3$ and $R_4$ will be branched.

In some embodiments, $R_3$ and $R_4$ can be $CH_3(CH_2)_yCH(CH_2)_x—$, where x is, independently for each occurrence, an integer selected from 0, 1, 2, 3, 4, 5, 6, 7, 8, 9, 10, 11, 12, 13, 14, 15, 16, 17, 18, 19, and 20, and y is, independently for each occurrence, an integer selected from 0, 1, 2, 3, 4, 5, 6, 7, 8, 9, 10, 11, 12, 13, 14, 15, 16, 17, 18, 19, and 20. Where both $R_3$ and $R_4$ are $CH_3(CH_2)_yCH(CH_2)_x—$, the compounds may be compounds according to Formula I and III.

Without being bound to any particular theory, in certain embodiments, altering the EN produces estolides having desired viscometric properties while substantially retaining or even reducing pour point. For example, in some embodiments estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil is accomplished by distillation, chromatography, membrane separation, phase separation, affinity separation, solvent extraction, or combinations thereof. In some embodiments, the distillation takes place at a temperature and/or pressure that is suitable to separate the estolide base oil into different "cuts" that individually exhibit different EN values. In some embodiments, this may be accomplished by subjecting the base oil to a temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

Typically, base stocks and lubricant compositions exhibit certain lubricity, viscosity, and/or pour point characteristics. For example, in certain embodiments, suitable viscosity characteristics of the base oil may range from about 10 cSt to about 250 cSt at 40° C., and/or about 3 cSt to about 30 cSt at 100° C. In some embodiments, the estolide base stocks may exhibit viscosities within a range from about 50 cSt to about 150 cSt at 40° C., and/or about 10 cSt to about 20 cSt at 100° C.

In some embodiments, estolide compounds and compositions may exhibit viscosities less than about 55 cSt at 40° C. or less than about 45 cSt at 40° C., and/or less than about 12 cSt at 100° C. or less than about 10 cSt at 100° C. In some embodiments, estolide compounds and compositions may exhibit viscosities less than about 40 cSt at 40° C. or less than about 30 cSt at 40° C., and/or less than about 8 cSt at 100° C. or less than about 6 cSt at 100° C. In some embodiments, estolide compounds and compositions may exhibit viscosities less than about 20 cSt at 40° C., and/or less than about 5 cSt at 100° C. In some embodiments, estolide compounds and compositions may exhibit viscosities within a range from about 15 cSt to about 25 cSt at 40° C., and/or about 3 cSt to about 6 cSt at 100° C. In some embodiments, estolide compounds and compositions may exhibit viscosities within a range from about 18 cSt to about 20 cSt at 40° C., and/or about 4 cSt to about 5 cSt at 100° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or 55 cSt at 40° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 25, or 30 cSt at 100° C.

In certain embodiments, estolides may exhibit desirable low-temperature pour point properties. In some embodiments, estolide compounds and compositions may exhibit a pour point lower than about −25° C., about −35° C., −40° C., or even about −50° C. In some embodiments, estolides have a pour point of about −25° C. to about −45° C. In some embodiments, the pour point falls within a range of about −30° C. to about −40° C., about −34° C. to about −38° C., about −30° C. to about −45° C., about −35° C. to about −45° C., 34° C. to about −42° C., about −38° C. to about −42° C., or about 36° C. to about −40° C. In some embodiments, the pour point falls within the range of about −27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C., about −37° C., about −38° C., about −39° C., about −40° C., about −41° C., about −42° C., about −43° C., about −44° C., or about −45° C. In some embodiments, the lower bound of the pour point is greater than about −70° C., about −69° C., about −68° C., about −67° C., about −66° C., about −65° C., about −64° C., about −63° C., about −62° C., about −61° C., about −60° C., about −59° C., about −58° C., about −57° C., about −56° C., about −55° C., about −54° C., about −53° C., about −52° C., −51, about −50° C., about −49° C., about −48° C., about −47° C., about −46° C., or about −45° C.

In addition, in certain embodiments, estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of estolides in an effort to increase the oil's oxidative stability, while also decreasing harmful deposits and the corrosiveness of the oil.

In some embodiments, estolides have an IV of less than about 40 cg/g or less than about 35 cg/g. In some embodiments, estolides have an IV of less than about 30 cg/g, less than about 25 cg/g, less than about 20 cg/g, less than about 15 cg/g, less than about 10 cg/g, or less than about 5 cg/g. The IV of an estolide may be reduced by decreasing the estolide's degree of unsaturation. In certain embodiments, this may be accomplished by, for example, increasing the amount of saturated capping materials relative to unsaturated capping materials when synthesizing the estolides. Alternatively, in certain embodiments, IV may be reduced by hydrogenating estolides having unsaturated caps.

In some embodiments, estolides comprise at least one compound of Formula II, wherein: one or more of $R_3$ and $R_4$ are selected from a saturated and unbranched $C_{1-7}$ alkyl; n is 1; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 2; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 3; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 4; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 5; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 6; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 7; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-7}$ alkyl; n is 8; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 1; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 2; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 3; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 4; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 5; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 6; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 7; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{21}$ alkyl; n is 8; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 1; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 2; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 3; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 4; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 5; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 6; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 7; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-5}$ alkyl; n is 8; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 1; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 2; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 3; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 4; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 5; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 6; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 7; and $R_2$ is an optionally substituted $C_1$-$C_{40}$ alkyl that is saturated or unsaturated and branched or unbranched.

In some embodiments, estolides comprise at least one compound of Formula II, wherein: one or more of $R_3$ and $R_4$ are selected from a saturated and unbranched $C_{1-9}$ alkyl; n is 8; and $R_2$ is an optionally substituted $C_1$-$C_{40}$ alkyl that is saturated or unsaturated and branched or unbranched.

The present disclosure further relates to methods of making estolides according to Formula I, II, and III. By way of example, the reaction of an unsaturated fatty acid with acetic acid and the esterification of the resulting free acid estolide are illustrated and discussed in the following Schemes 1 and 2. The particular structural formulas used to illustrate the reactions correspond to those for synthesis of compounds according to Formula I and III; however, the methods apply equally to the synthesis of compounds according to Formula II, with use of compounds having structure corresponding to $R_3$ and $R_4$ with a reactive site of unsaturation.

As illustrated below, compound 100 represents an unsaturated fatty acid that may serve as the basis for preparing the estolide compounds described herein.

Scheme 1

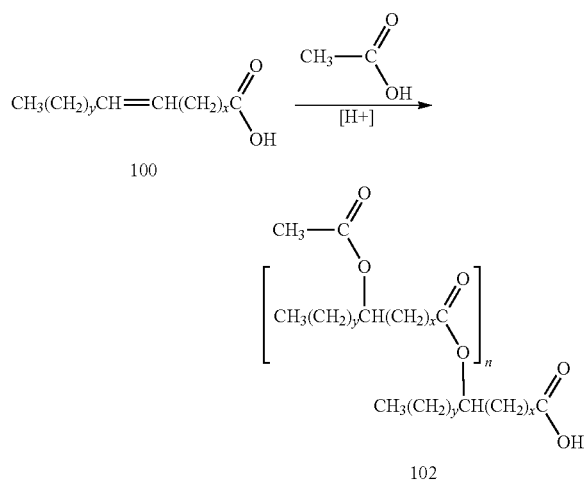

100

102

In Scheme 1, wherein x is, independently for each occurrence, an integer selected from 0 to 20, y is, independently for each occurrence, an integer selected from 0 to 20, and n is an integer greater than or equal to 1, unsaturated fatty acid 100 may be combined with acetic acid and a proton from a proton source to form free acid estolide 102. Any suitable proton source may be implemented to catalyze the formation of free acid estolide 102, including but not limited to homogenous acids and/or strong acids like hydrochloric acid, sulfuric acid, perchloric acid, nitric acid, triflic acid, and the like. In certain embodiments, free acid estolides may be esterified to form an ester product using any suitable method known to those of skill in the art, including but not limited to homogenous acids and/or strong acids like hydrochloric acid, sulfuric acid, perchloric acid, nitric acid, triflic acid, and the like.

Scheme 2

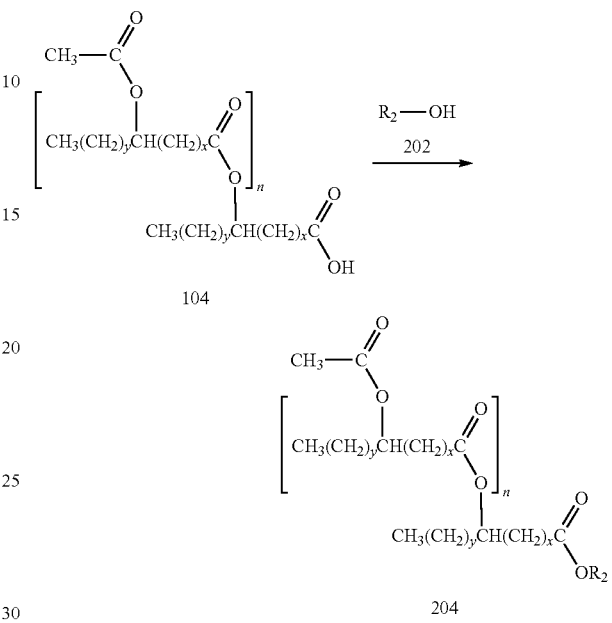

104

204

Similarly, in Scheme 2, wherein x is, independently for each occurrence, an integer selected from 0 to 20, y is, independently for each occurrence, an integer selected from 0 to 20, and n is an integer greater than or equal to 1, free acid estolide 104 may be esterified by any suitable procedure known to those of skilled in the art, such as acid-catalyzed reduction with alcohol 202, to yield esterified estolide 204. Other exemplary methods may include other types of Fischer esterification, such as those using Lewis acid catalysts such as $BF_3$.

As discussed above, in certain embodiments, the estolides described herein may have improved properties which render them useful as base stocks for biodegradable lubricant applications. Such applications may include, without limitation, crankcase oils, gearbox oils, hydraulic fluids, drilling fluids, two-cycle engine oils, greases, dielectric fluids, and the like. Other suitable uses may include marine applications, where biodegradability and toxicity are of concern. In certain embodiments, the nontoxic nature of certain estolides described herein may also make them suitable for use as lubricants in the cosmetic and food industries.

In certain embodiments, estolide compounds may meet or exceed one or more of the specifications for certain end-use applications, without the need for conventional additives. For example, in certain instances, high-viscosity lubricants, such as those exhibiting a kinematic viscosity of greater than about 120 cSt at 40° C., or even greater than about 200 cSt at 40° C., may be desirable for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising an estolide base stock. For example, in certain embodiments, the estolides described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the estolides described herein may be co-blended with one or more synthetic or petroleum-based oils to achieve the desired viscosity and/or pour point profiles. In certain embodiments, certain estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:

NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1H$ NMR by a peak at about 4.84 ppm.

Estolide Number (EN):

The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):

The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I, II, and III, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:

The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):

GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:

To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \sum 100 \times \frac{A_f \times MW_I \times db}{MW_f}$$

$A_f$=fraction of fatty compound in the sample
$MW_I$=253.81, atomic weight of two iodine atoms added to a double bond
db=number of double bonds on the fatty compound
$MW_f$=molecular weight of the fatty compound The properties of exemplary estolide compounds and compositions described herein are identified in Tables 1-4.

Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat#244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 torr) to remove all monoester material leaving behind estolides.

Example 2

The acid catalyst reaction was conducted in a glass reaction vessel. Oleic acid (1 equiv., OL 700, Twin Rivers) was added to the vessel with 70% perchloric acid (Aldrich Cat#244252) and acetic acid (2 equiv.), and heated to 60° C. in vacuo (10 torr abs) for 24 hrs while continuously being agitated. After 24 hours the vacuum was released. 2-Ethylhexanol (2-EH) (1 equiv.) was then added to the reactor and the vacuum was restored. The reaction was allowed to continue under the same conditions (60° C., 10 torr abs) for 4 more hours. At which time, KOH (1.2 equiv.) was dissolved in 90% ethanol/water (9:1) and added to the vessel to quench the acid. The solution was then allowed to cool for approximately 30 minutes. The contents of the reactor were then pumped through a 1μ filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the vessel. The vessel was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Kugelrohr still at 110° C. under an absolute pressure in vacuo (10 torr abs) for 3 hrs, and then at 110° C. under an absolute pressure in vacuo (10 torr abs) for 3 hrs, to collect the distillates and residues. The properties of resulting products are set forth below:

| | $HClO_4$ equiv. | Pour Point (° C.) | Cloud Point (° C.) | Visc. (40° C.) | Visc. (100° C.) | Visc. Index | Acid Value (mg KOH/g) | Gardner Color |
|---|---|---|---|---|---|---|---|---|
| 1 | 0.05 | −15 | −15 | 112.7 | 16.8 | 162 | 3.82 | 16 |
| 2 | 0.017 | −39 | −39 | 102 | 15.8 | 165 | 7.98 | 14 |
| 3* | 0.017 | −40 | — | 19.9 | 4.8 | 174 | 0.95 | — |
| 4 | 0.05 | −42 | <−42 | 79.1 | 12.5 | 156 | 4.47 | 15+ |

*Starting material comprised estolide product of Example 2 (1 equiv.) re-esterified with $BF_3 \cdot OEt_2$ (0.15 equiv.) and 2-EH (1 equiv.) in a reaction vessel equipped with a Dean-Stark trap and heated to 80° C. in vacuo (10 torr abs) for 12 hours.

Example 3

Estolides according to Formula I, II, and III are prepared in a manner substantially similar to those set forth in Example 2, except the 2-ethylhexanol esterifying alcohol is replaced with various alcohols, including those identified below.

| Alcohol | Structure |
|---|---|
| Jarcol ™ I-18CG | iso-octadecanol |
| Jarcol ™ I-12 | 2-butyloctanol |
| Jarcol ™ I-20 | 2-octyldodecanol |
| Jarcol ™ I-16 | 2-hexyldecanol |
| Jarcol ™ 85BJ | cis-9-octadecen-1-ol |
| Fineoxocol ® 180 | $CH_3-\underset{\underset{CH_3}{\vert}}{\overset{\overset{CH_3}{\vert}}{C}}-CH_2-\underset{\underset{CH_3-\underset{\underset{CH_3}{\vert}}{\overset{\overset{CH_3}{\vert}}{C}}-CH_2-CH}{\vert}}{\overset{\overset{CH_3}{\vert}}{CH}}-(CH_2)_2-CH-CH_2OH$ |
| Jarcol ™ I-18T | 2-octyldecanol |

Example 4

Estolides of Formula I, II, and III are prepared in a manner substantially similar to those set forth in Example 2, except the 2-ethylhexanol esterifying alcohol is replaced with various alcohols, including those set forth below, which may be saturated or unsaturated and unbranched or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched or unbranched residue at the $R_2$ position:

| Alcohol | $R_2$ Substituents |
|---|---|
| $C_1$ alkanol | methyl |
| $C_2$ alkanol | ethyl |
| $C_3$ alkanol | n-propyl, isopropyl |
| $C_4$ alkanol | n-butyl, isobutyl, sec-butyl |
| $C_5$ alkanol | n-pentyl, isopentyl neopentyl |
| $C_6$ alkanol | n-hexyl, 2-methyl pentyl, 3-methyl pentyl, 2,2-dimethyl butyl, 2,3-dimethyl butyl |
| $C_7$ alkanol | n-heptyl and other structural isomers |
| $C_8$ alkanol | n-octyl and other structural isomers |
| $C_9$ alkanol | n-nonyl and other structural isomers |
| $C_{10}$ alkanol | n-decanyl and other structural isomers |
| $C_{11}$ alkanol | n-undecanyl and other structural isomers |
| $C_{12}$ alkanol | n-dodecanyl and other structural isomers |
| $C_{13}$ alkanol | n-tridecanyl and other structural isomers |
| $C_{14}$ alkanol | n-tetradecanyl and other structural isomers |
| $C_{15}$ alkanol | n-pentadecanyl and other structural isomers |
| $C_{16}$ alkanol | n-hexadecanyl and other structural isomers |
| $C_{17}$ alkanol | n-heptadecanyl and other structural isomers |
| $C_{18}$ alkanol | n-octadecanyl and other structural isomers |
| $C_{19}$ alkanol | n-nonadecanyl and other structural isomers |
| $C_{20}$ alkanol | n-icosanyl and other structural isomers |
| $C_{21}$ alkanol | n-heneicosanyl and other structural isomers |
| $C_{22}$ alkanol | n-docosanyl and other structural isomers |

Example 5

"Ready" and "ultimate" biodegradability of the estolide produced in Example 1 was tested according to standard OECD procedures. Results of the OECD biodegradability studies are set forth below:

| | 301D 28-Day (% degraded) | 302D Assay (% degraded) |
|---|---|---|
| Canola Oil | 86.9 | 78.9 |
| Ex. 1 Base Stock | 64.0 | 70.9 |

Example 6

The Ex. 1 estolide base stock was tested under OECD 203 for Acute Aquatic Toxicity. The tests showed that the estolides are nontoxic, as no deaths were reported for concentration ranges of 5,000 mg/L and 50,000 mg/L.

The invention claimed is:

1. A composition comprising at least one compound of Formula I:

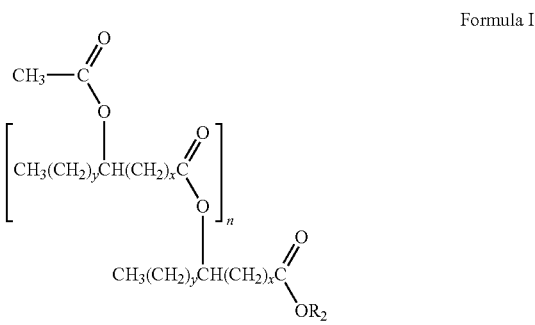

Formula I wherein
x is, independently for each occurrence, an integer selected from 7 and 8;
y is, independently for each occurrence, an integer selected from 7 and 8;
n is an integer selected from 1 to 20; and
$R_2$ is selected from hydrogen and optionally substituted alkyl that is saturated or unsaturated, and branched or unbranched;
wherein each fatty acid chain residue of said at least one compound is independently optionally substituted.

2. The composition according to claim 1, wherein
n is an integer selected from 1 to 12; and
$R_2$ is optionally substituted $C_1$ to $C_{22}$ alkyl that is saturated or unsaturated, and branched or unbranched,
wherein each fatty acid chain residue is unsubstituted.

3. The composition according to claim 2, wherein n is an integer selected from 1 to 6.

4. The composition according to claim 1, wherein x+y is 15 for each fatty acid chain residue of the at least one compound of Formula I.

5. The composition according to claim 1, wherein $R_2$ is a branched or unbranched $C_1$ to $C_{20}$ alkyl that is unsubstituted, and saturated or unsaturated.

6. The composition according to claim 5, wherein $R_2$ is saturated.

7. The composition according to claim 6, wherein $R_2$ is a branched $C_6$ to $C_{12}$ alkyl.

8. The composition according to claim 7, wherein $R_2$ is 2-ethylhexyl.

9. The composition according to claim 1, wherein said composition has an EN selected from an integer or fraction of an integer that is equal to or greater than 2, a kinematic viscosity equal to or less than 5 cSt when measured at 100° C. and/or equal to or less than 20 cSt when measured at 40° C., and a pour point equal to or lower than −36° C., wherein the EN is the average number of estolide linkages in compounds according to Formula I.

10. The composition according to claim 1, wherein said composition has an EN that is an integer or fraction of an integer selected from 2 to 3, wherein the EN is the average number of estolide linkages in compounds according to Formula I.

11. The composition according to claim 1, wherein said composition has a kinematic viscosity within a range from 18 cSt to 20 cSt at 40° C., and/or 4 cSt to 5 cSt at 100° C.

12. The composition according to claim 1, wherein said composition exhibits a pour point of −38° C. to −42° C.

13. The composition according to claim 1, wherein said composition comprises two or more compounds of Formula I.

14. The composition according to claim 1, wherein said composition consists essentially of two or more compounds of Formula I.

15. The composition according to claim 1, wherein n is 1.

16. The composition according to claim 4, wherein $R_2$ is a branched or unbranched $C_1$ to $C_{20}$ alkyl that is unsubstituted, and saturated or unsaturated.

17. The composition according to claim 16, wherein $R_2$ is saturated.

18. The composition according to claim 17, wherein $R_2$ is branched.

* * * * *